(12) United States Patent
Biondi et al.

(10) Patent No.: US 9,081,903 B2
(45) Date of Patent: Jul. 14, 2015

(54) INTERFACE DEVICE FOR COMMUNICATION BETWEEN A MEDICAL DEVICE AND A COMPUTER

(75) Inventors: James W. Biondi, North Haven, CT (US); Michael G. Engler, Stamford, CT (US); Mark Joseph Tuccillo, Southington, CT (US)

(73) Assignee: IVY BIOMEDICAL SYSTEMS, INC., Branford, CT (US)

( * ) Notice: Subject to any disclaimer, the term of this patent is extended or adjusted under 35 U.S.C. 154(b) by 0 days.

(21) Appl. No.: 13/335,198

(22) Filed: Dec. 22, 2011

(65) Prior Publication Data

US 2012/0102339 A1 Apr. 26, 2012

Related U.S. Application Data

(63) Continuation of application No. 12/694,148, filed on Jan. 26, 2010, now abandoned.

(60) Provisional application No. 61/148,259, filed on Jan. 29, 2009.

(51) Int. Cl.
 *G06F 19/00* (2011.01)
 *A61B 5/145* (2006.01)
 *G06F 13/38* (2006.01)

(52) U.S. Cl.
 CPC .......... *G06F 13/385* (2013.01); *A61B 5/14532* (2013.01); *G06F 19/3418* (2013.01)

(58) Field of Classification Search
None
See application file for complete search history.

(56) References Cited

U.S. PATENT DOCUMENTS

| | | | |
|---|---|---|---|
| 5,325,395 A * | 6/1994 | Tran | 375/219 |
| 5,473,229 A * | 12/1995 | Archer et al. | 318/400.18 |
| 5,579,775 A * | 12/1996 | Dempsey et al. | 600/483 |
| 5,751,823 A * | 5/1998 | Strickland et al. | 381/94.6 |
| 5,755,742 A * | 5/1998 | Schuelke et al. | 607/27 |
| 6,233,640 B1 | 5/2001 | Luke et al. | |
| 6,263,245 B1 * | 7/2001 | Snell | 607/60 |
| 6,915,142 B1 | 7/2005 | Wietfeldt | |
| 6,931,464 B1 * | 8/2005 | Reeves | 710/62 |
| 7,369,156 B1 | 5/2008 | Heinke et al. | |

(Continued)

FOREIGN PATENT DOCUMENTS

| | | |
|---|---|---|
| JP | 07-175746 | 7/1995 |
| JP | 2003-233445 | 8/2003 |

(Continued)

OTHER PUBLICATIONS

B&B Electronics, Quatech Model SSU2-400I Operation Manual (USB to RS-232/422/485 Isolated Converter, Jun. 2008, First Edition, http://www.bb-elec.com/Products/Manuals/SSU2-400I_manual-pdf.pdf.*

(Continued)

*Primary Examiner* — Moustafa M Meky
*Assistant Examiner* — Ho Shiu
(74) *Attorney, Agent, or Firm* — K&L Gates LLP

(57) ABSTRACT

The present invention relates to an interface device and a method for communication between a medical device and a computer system. In some embodiments, the interface device comprises a conversion device and/or a processor-transceiver and a memory in electrical communication with the conversion device, wherein the memory contains data to instruct the conversion device and/or the processor transceiver how to communicate with the medical device.

10 Claims, 5 Drawing Sheets

(56) References Cited

U.S. PATENT DOCUMENTS

| | | |
|---|---|---|
| 7,574,589 B1 | 8/2009 | Jaswa et al. |
| 7,667,353 B2 * | 2/2010 | Coolidge et al. .............. 307/127 |
| 7,720,639 B2 | 5/2010 | Kirchner et al. |
| 7,778,244 B1 | 8/2010 | Sheikh et al. |
| 8,452,380 B2 * | 5/2013 | Williams et al. .............. 600/432 |
| 2001/0047441 A1 | 11/2001 | Robertson |
| 2002/0007198 A1 * | 1/2002 | Haupert et al. ................. 607/30 |
| 2002/0151990 A1 * | 10/2002 | Ulrich et al. .................... 700/65 |
| 2003/0033457 A1 | 2/2003 | Faist |
| 2003/0179818 A1 * | 9/2003 | D'Angelo et al. ............ 375/222 |
| 2003/0188049 A1 * | 10/2003 | Dickens ........................... 710/8 |
| 2004/0100854 A1 * | 5/2004 | Rahamim et al. ............. 365/232 |
| 2004/0103234 A1 | 5/2004 | Zer et al. |
| 2004/0116967 A1 * | 6/2004 | DeGroot et al. .................. 607/5 |
| 2005/0001179 A1 * | 1/2005 | Gisler et al. .................. 250/551 |
| 2005/0057219 A1 * | 3/2005 | Kaminski et al. ............. 320/116 |
| 2005/0068427 A1 * | 3/2005 | Sudo et al. ................. 348/222.1 |
| 2005/0102167 A1 * | 5/2005 | Kapoor ............................. 705/3 |
| 2005/0106941 A1 * | 5/2005 | Witchey ........................ 439/620 |
| 2005/0156583 A1 * | 7/2005 | Nachamiev et al. .......... 323/283 |
| 2005/0187732 A1 | 8/2005 | Rauer et al. |
| 2005/0192645 A1 * | 9/2005 | Stein et al. ..................... 607/49 |
| 2005/0268006 A1 * | 12/2005 | Julicher et al. ................ 710/62 |
| 2006/0025684 A1 * | 2/2006 | Quistgaard et al. ........... 600/441 |
| 2006/0025830 A1 * | 2/2006 | Freeberg ........................ 607/32 |
| 2006/0055379 A1 * | 3/2006 | Yamamoto et al. ........... 323/212 |
| 2007/0043981 A1 * | 2/2007 | Wu et al. ......................... 714/49 |
| 2007/0247310 A1 * | 10/2007 | Ulrich et al. .................. 340/540 |
| 2007/0255348 A1 * | 11/2007 | Holtzclaw ...................... 607/60 |
| 2007/0258395 A1 * | 11/2007 | Jollota et al. ................. 370/310 |
| 2007/0282389 A1 | 12/2007 | Moxon et al. |
| 2007/0293183 A1 * | 12/2007 | Marlowe ........................ 455/345 |
| 2008/0004904 A1 * | 1/2008 | Tran ................................. 705/2 |
| 2008/0031450 A1 * | 2/2008 | Yamashita .................... 380/212 |
| 2008/0146925 A1 * | 6/2008 | Byrd et al. .................... 600/438 |
| 2008/0146940 A1 * | 6/2008 | Jenkins et al. ................ 600/463 |
| 2008/0184806 A1 | 8/2008 | Valentini |
| 2008/0192509 A1 * | 8/2008 | Dhuyvetter et al. ............ 363/17 |
| 2008/0200827 A1 * | 8/2008 | Cyphery et al. .............. 600/546 |
| 2008/0222711 A1 | 9/2008 | Michaelis |
| 2008/0250147 A1 | 10/2008 | Knibbeler et al. |
| 2008/0250179 A1 | 10/2008 | Moon |
| 2008/0277761 A1 * | 11/2008 | Mahalingam et al. ........ 257/532 |
| 2008/0317106 A1 * | 12/2008 | Leung et al. .................. 375/220 |
| 2009/0013111 A1 | 1/2009 | Berland et al. |
| 2009/0030476 A1 * | 1/2009 | Hargrove ........................ 607/40 |
| 2009/0115628 A1 * | 5/2009 | Dicks et al. ............. 340/870.07 |
| 2009/0120810 A1 * | 5/2009 | Phan et al. ..................... 205/792 |
| 2009/0132070 A1 | 5/2009 | Ebrom et al. |
| 2009/0149254 A1 | 6/2009 | Kelly et al. |
| 2009/0181286 A1 * | 7/2009 | Brunner et al. ................. 429/50 |
| 2009/0228623 A1 * | 9/2009 | Tsuchiya ........................ 710/72 |
| 2009/0281597 A1 | 11/2009 | Parramon et al. |
| 2009/0287065 A1 * | 11/2009 | Yamaki et al. ................ 600/300 |
| 2009/0312694 A1 * | 12/2009 | Bedingfield et al. ........... 604/29 |
| 2009/0323717 A1 * | 12/2009 | Landry et al. ................. 370/463 |

FOREIGN PATENT DOCUMENTS

| | | |
|---|---|---|
| JP | 2004-020976 | 1/2004 |
| JP | 2006-221485 | 8/2006 |
| JP | 2007-323464 | 12/2007 |
| WO | 2005122711 A2 | 12/2005 |
| WO | 2007114656 A1 | 10/2007 |
| WO | 2008/118204 A2 | 10/2008 |

OTHER PUBLICATIONS

USB Implementers Forum: "Wireless Universal Serial Bus Specification, Revision 1.0" May 12, 2005, pp. i-18.

International Search Report for International Application No. PCT/US2010/022131, mailed Apr. 26, 2010, 4 pgs.

Written Opinion of the International Searching Authority for International Application No. PCT/US2010/022131, mailed Apr. 26, 2010, 3 pgs.

Office Action for Israeli Patent Application No. 214339, dated Feb. 17, 2015, 5 pgs.

* cited by examiner

INTERFACE DEVICE FOR COMMUNICATION BETWEEN A MEDICAL DEVICE AND A COMPUTER

CROSS REFERENCE TO RELATED APPLICATIONS

This application is a continuation of U.S. patent application Ser. No. 12/694,148, filed on Jan. 26, 2010, which claims priority to and the benefit of U.S. Provisional Patent Application No. 61/148,259, filed on Jan. 29, 2009, the entire disclosures of each of which are incorporated by reference herein.

FIELD OF THE INVENTION

The present invention relates to an interface device for communication between a medical device and a network.

BACKGROUND OF THE INVENTION

In a hospital, patients' vital signs are monitored by numerous electronic devices. Each one of these devices produces its own set of data with its own format that must be compiled and analyzed. In order to record all of this vital information, the electronic devices need to communicate with a computer system. However, the computer system may not be able to communicate with the various electronic devices because the computer's communication protocol may differ from that of the electronic device.

Therefore, a need exists for a system where a medical device can communicate with a computer system for recording and compiling patient information.

SUMMARY OF THE INVENTION

In satisfaction of these needs and others, the present invention relates to an interface device to facilitate communication between a medical device and a bridge. In one aspect, the present invention relates to the interface device comprising an interface device and a memory in electrical communication with the interface device, wherein the memory contains data to instruct the interface device how to communicate with the medical device. In other embodiments, the interface device can include an RS232 transceiver, a solid state isolator, and/or an isolated power supply having a power control circuit, each in electrical communication with the interface device.

Another aspect of the present invention relates to a system for communication between a computer and a medical device. In one embodiment, the system comprises a bridge, a USB/RS232 circuit in electrical communication with the bridge, a memory in electrical communication with the USB/RS232 circuit, and the medical device in electrical communication with the USB/RS232 circuit, wherein the memory contains data to instruct the USB/RS232 circuit on how to communicate with the medical device.

Another aspect of the present invention relates to a method of communicating between a medical device and a bridge, comprising the steps of storing communication data to identify and communicate with the medical device, receiving medical device data from the medical device, and using the communication data to communicate with the medical device and to convert medical device data from the medical device to permit the medical device to communicate with the bridge.

Another aspect of the present invention relates to a wireless interface device for communication between an medical device and a bridge including a processor-transceiver, a memory in electrical communication with the processor-transceiver, and a wireless transmitter in electrical communication with the processor-transceiver and in wireless communication with the bridge, wherein the memory contains communication data to instruct the processor-transceiver how to communicate with the medical device. The processor-transceiver can include a micro-controller.

Another aspect of the present invention relates to a system for communication between a computer and an medical device including a bridge, a processor-transceiver in wireless communication with the bridge, a memory in electrical communication with the processor-transceiver, and the medical device in electrical communication with the processor-transceiver, wherein the memory contains communication data to instruct the processor-transceiver on how to communicate with the medical device.

Another aspect of the present invention relates to a method of communicating between an medical device and a bridge including the steps of: storing communication data to communicate with the medical device, receiving medical device data from the medical device, using the communication data to convert medical device data from the medical device to permit the medical device to communicate with the bridge, and transmitting the communication data wirelessly to the bridge.

Another aspect of the present invention relates to a system for communication between a medical device and a bridge including a medical device, a conversion circuit in electrical communication with the medical device, a processor-transceiver in electrical communication with the medical device, an antenna in electrical communication with the processor-transceiver, a multiplexer in electrical communication with both the conversion circuit and the processor-transceiver, and a memory in electrical communication with the multiplexer, wherein the multiplexer permits either the conversion circuit or the processor-transceiver to communicate with the memory, and wherein the memory contains communication data to instruct the processor-transceiver on how to communicate with the medical device.

BRIEF DESCRIPTION OF THE DRAWINGS

These embodiments and other aspects of this invention will be readily apparent from the description below and the appended drawings, which are meant to illustrate and not to limit the invention, and in which.

DESCRIPTION

The present invention will be more completely understood through the following description, which should be read in conjunction with the attached drawings. In this description, like numbers refer to similar elements within various, embodiments of the present invention. Within this description, the claimed invention will be explained with respect to embodiments. However, the skilled artisan will readily appreciate that the methods and systems described herein are, merely, exemplary and that variations can be made without departing from the spirit and scope of the invention.

Figure 1:
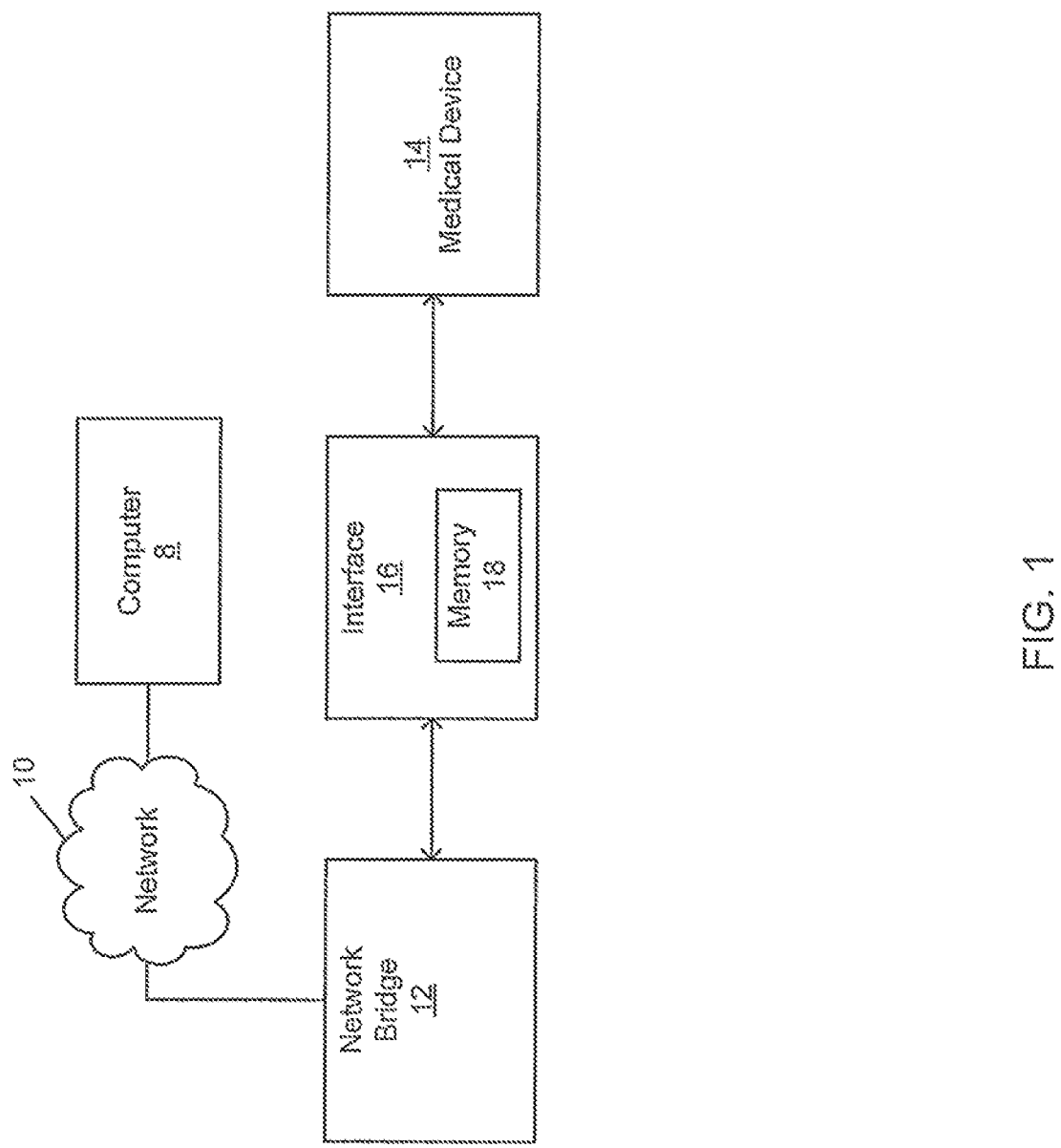
FIG. 1 is a block diagram illustrating a system for connecting to bridge and an medical device through an interface device, according to an embodiment of the present invention.

In general, and referring to FIG. 1, the present invention relates to an interface device 16 to facilitate communication between a medical device 14 and a computer system. As shown in FIG. 1 such a system includes a computer 8 in communication with a network 10. Also in communication with the network 10 are one or more bridges 12 that permit medical devices 14 to communicate with the network 10. Typical bridges 12 have one or more uniform input ports that are frequently Universal Serial Bus ports (USB ports) and an output port (for example an ethernet port) which is configured to communicate with the network 10 to which the bridge 12 is attached. Unfortunately, most medical devices 14 have output ports which are RS232 compatible serial ports and which produce only RS232 compatible output signals. The medical device can be pulse oximeters, ventilators, EKG devices, and various other health-related monitoring devices.

These medical devices 14 use data transmission protocols which are specific to the individual medical device 14. As a result, there is both an electrical and protocol mismatch between the medical device 14 and the bridge 12. To best permit the medical device 14 to communicate with the bridge 12 without requiring the bridge 12 to accept and recognize all forms of communication signals and protocols, an interface device 16 is placed between the medical device 14 and the bridge 12.

This interface device 16 is then programmed to communicate with each medical device 14 to which it is connected. The interface device 16, sometimes referred to as a dongle, is a small hardware device that has a proper electrical or wireless port (e.g. RS232 serial port) to connect to the medical device 14 and a second port that is the correct electrical port (e.g. USB port) to communicate with the bridge 12.

Figure 2:
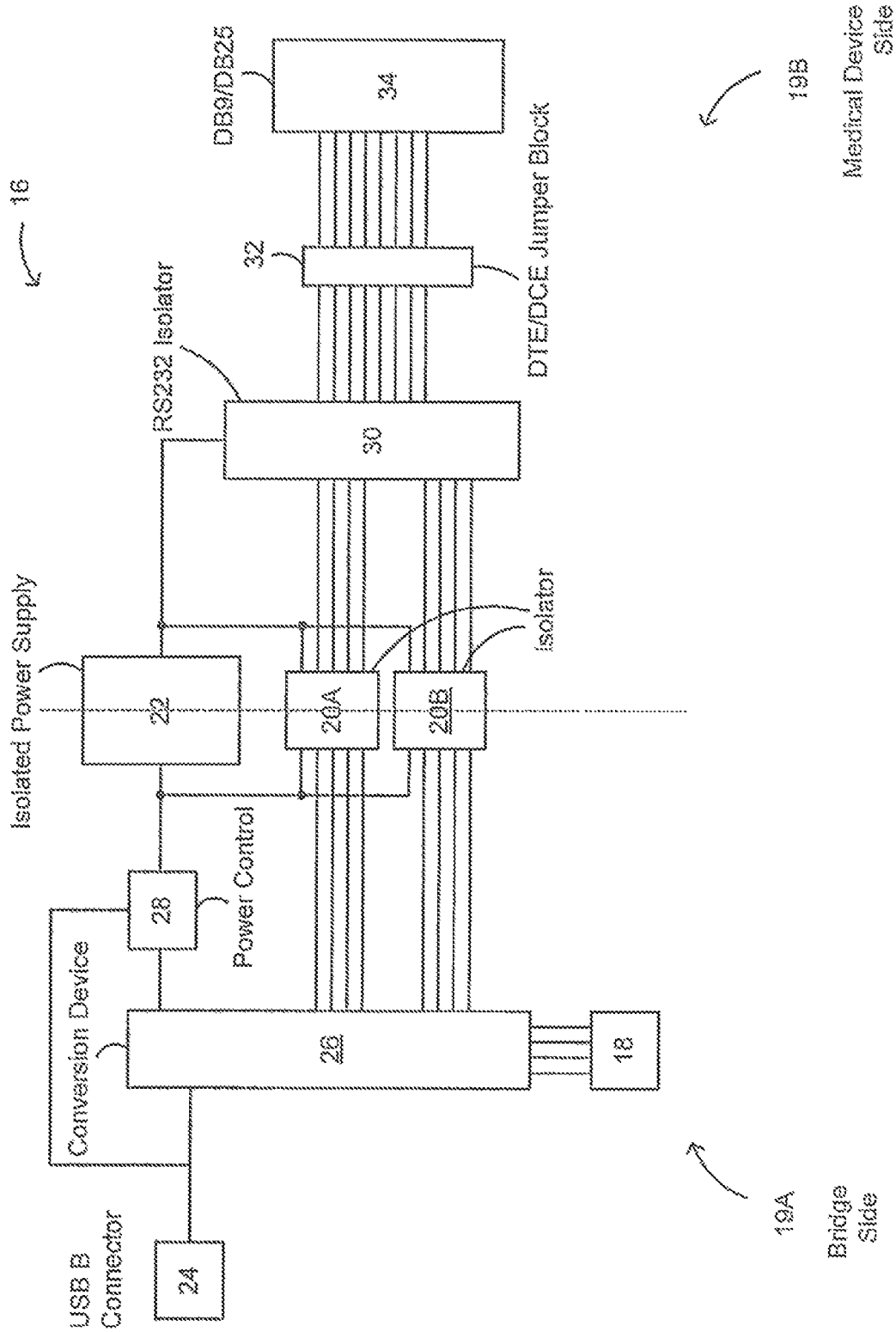
FIG. 2 is a block diagram of an embodiment of the interface device according to the present invention.

In more detail and as shown in FIG. 2, the interface device 16 may be considered to have a bridge side 19A and a medical device side 19B which are connected together through one or more isolators 20A, 20B (generally 20) and a conversion circuit 26. The isolators are electrical safety devices to provide electrical isolation between the bridge and the medical device, (and hence the patient to which the device 14 is connected). In various embodiments, the isolators 20 are optical isolators or galvimetric isolators.

A conversion circuit 26 converts the data received from the medical device 14 to data usable by the bridge 12 and sends that data to the bridge 12 through a connector 24, and vice versa. In one embodiment, the conversion circuit 26 is a USB/RS232 circuit, which converts the RS232 serial signals from the medical device 14 to USB signals usable by the bridge 12 and USB signals from the bridge 12 to RS232 signals usable by the medical device 14

In general, signals passing from the medical device 14 pass through the isolators 20A and 20B, before entering the conversion circuit 26 for conversion to USB signals. Similarly, signals entering the conversion circuit 26 from the bridge 12 pass through the isolators 20A, 20B before passing to the medical device 14. However, for some electronic devices, the medical device data cannot be converted to bridge data that the bridge 12 can process unless the data is recognized and converted by the conversion circuit 26. Instructions on how to convert and modify the medical device data (such as RS232 serial data) into bridge data (such as USB data) is stored in the memory 18 which is connected to the conversion circuit device 26 and is provided to the conversion circuit 26 when the interface 16 is initially powered on.

The memory 18 in one embodiment is an Electrically Erasable Programmable Read-Only Memory ("EEPROM"). The EEPROM can have a memory of from 256 bytes to 512 bytes. The memory 18 in one embodiment typically is contained within the interface device 16. The memory 18 is programmed to identify and communicate with various electronic devices. For example, the memory 18 of the interface device 16 is generally programmed prior to its connection with the intended medical device, for example, a ventilator. When the interface device 16 is the connected between the ventilator and to the bridge 12, the memory 18 of the interface device 16 is already programmed to permit the bridge 12 to communicate with the ventilator.

The interface 16 also includes an isolated power supply 22 and power controller 28. The isolated power supply 22 powers the components of the interface device 16 and is also constructed to electrically isolate the bridge 12 from the medical device 14. In one embodiment, the isolated power supply 22 includes a 4,000 volt, pulse-width-modulated power supply constructed with a triply insulated transformer. The power controller 28 controls the power to the USB/RS232 circuit and the other components of the interface 16. The isolated power supply 22 is discussed in more detail below.

In one embodiment, an RS232 transceiver 30, a RS232 DTE/DCE jumper block 32 and a DB9/DB25 connector are located between the medical device 14 and the isolators 20A, 20B. The RS232 transceiver is a standard RS232 transceiver, with ports in communication with the isolators 20A and 20B, and ports in communication with the DTE/DCE jumper block 32. The data terminal equipment/data circuit-terminating ("DTE/DCE") juniper block 32 enables the transmission and reception of signals to and from different pins in the. DB9/DB25 connector 34.

In operation, the first step is the storing in the memory 18 of device communication data that instructs the conversion circuit 26 how to communicate with the medical device 14. Typically, the communication data is stored on the interface device 16 prior to the interface device 16 being attached to the medical device 14 or bridge 12. For example, a hospital technician identifies that an interface device 16 will be connected to a ventilator and programs the device communication data into the memory 18 of the interface device 16. The data and protocol enables the interface device 16 to convert the ventilator data into a form that is readable by the bridge 12 and the computer system 8.

Once the interface device 16 has the necessary communication data stored in its memory to permit the bridge 12 to communicate with the medical device 14, the interface device 16 begins receiving device data from the medical device 14. Once the interface device 16 starts receiving the medical device data, the conversion circuit 26 of the interface device 16 begins using the stored data and protocol to convert the medical device data received from the medical device 14 to permit the medical device 14 to communicate with the bridge 12.

Figure 3:
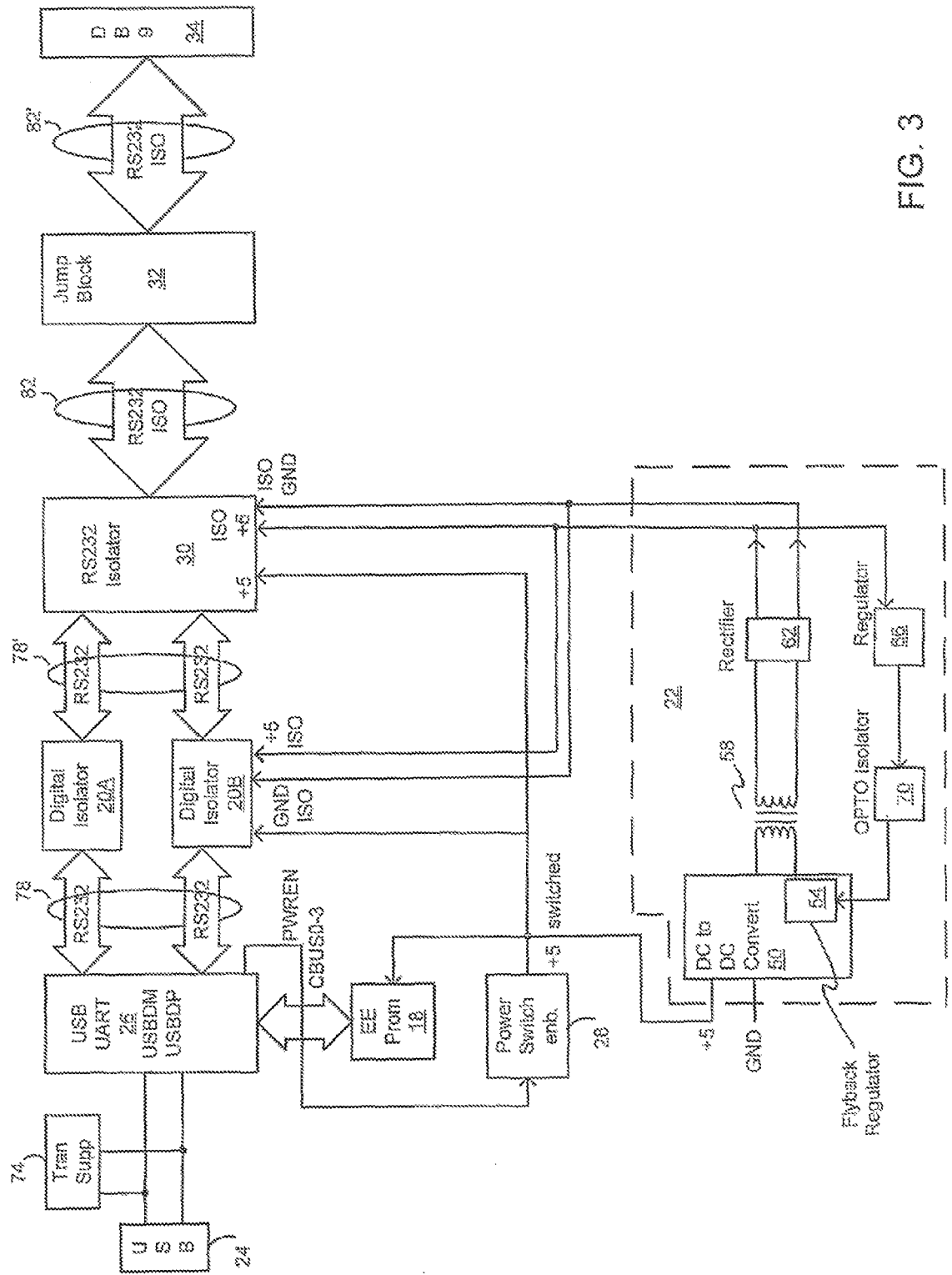
FIG. 3 is a more detailed diagram of an embodiment of the invention in FIG. 2.

Referring now to FIG. 3, a more detailed block diagram of the embodiment of an embodiment of the invention shown in FIG. 2 is shown. An important feature of the interface device. 16 is the electrical isolation it provides between the bridge 12 and the medical device 14. As shown in FIG. 3, one portion of this electrical isolation is provided by the isolated power supply 22. The isolated power supply 22 includes a DC to DC converter 50 which uses a flyback regulator 54 to produce a pulsed DC voltage from a static 5 volt DC source. In one embodiment, the flyback regulator is a National Semiconductor LM2587 (National Semiconductor, Santa Clara, Calif.).

This pulsed DC voltage causes a pulsed current to pass through isolation transformer 58 before being rectified by a rectifier circuit 62 to 5 volts. The isolation transformer 58 is wound with triply insulated wire to avoid insulation breakdown. The output of the rectifier circuit 62 is sampled by a regulator 66 whose output controls the flyback regulator 54 through an opto-isolator 70. In this way the voltage output from rectifier circuit 62 is isolated and regulated to 5 volts. In one embodiment, the regulator 66 is a National Semiconductor LM3411 (National Semiconductor, Santa Clara, Calif.) and the opto-isolator is an Agilent CNY17 (Agilent Technologies, Santa Clara, Calif.). The rectifier 62 in one embodiment is a discrete component half wave rectifier which is filtered to static DC. In one embodiment, the DC to DC converter is a discrete component converter. The regulated isolated 5 volts is then supplied to the components on the isolated side (medical device side) of the interface device 16.

As shown in FIG. 3, the USB connector 24 is connected to a USB UART (universal asynchronous receiver transmitter) conversion circuit 26 by way the input ports USBDM and USBDP. In one embodiment, the conversion circuit 26 is an FTDI FT232R USB UART integrated circuit (Future Technology Devices International Ltd, Glasgow, Scotland, United Kingdom). A transient suppressor 74 is connected across the USB ports to provide noise transient protection. In one embodiment, the suppressor 74 is a TI SN65220 universal serial bus port transient suppressor (Texas Instruments, Dallas, Tex.). The output ports 78 of the interface device 26 convey various signals to support an RS232 communication protocol.

One output line of the interface device 26 is a power enable pin which is used to control a power switch 28. In one embodiment, the power switch 28 is a MIC2026 power distribution switch (Micrel Inc, San Jose, Calif.)

The output of the power switch 28 is a 5 volt switched source which connects to the memory 18, the RS232 isolator 30 and the digital isolator 20A, 20B (only one shown connected for clarity) and the DC to DC converter 50. In one embodiment, the memory is an EEPROM AT93C56 (Atmel Corporation, San Jose, Calif.). The memory is connected to the switch 28 output by the Vcc pin of the memory 18. The output of the memory 18 CBUS0-CBUS3 is connected to pins. GPI0-GPI3 of the interface device 26. In operation, until the USB UART 26 is fully enabled, the switch 28 prevents any of the powered components to which the switch 28 is connected from being fully powered.

The RS232 lines 78 are connected to the RS232 isolator 30 through the digital isolators 20A and 20B. In one embodiment, the digital isolators 30 are ADµM2400 digital isolators (Analog Devices, Norwood, Mass.). These digital isolators electrically isolate the signals passing between the interface conversion circuit 26 and the RS232 isolator 30. In one embodiment, the RS232 isolator is an ADM213E 15 kV ESD-Protected RS-232 Line Driver/Receiver (Analog Devices, Norwood, Mass.). The RS232 isolator 30 further isolates the RS232 signals to form isolated RS232 signals 82 which are then input to the jumper block 32. The jumper block 32 connects the RS232 isolator 30 to the DB9 connector 34 and allows the correct signals to be jumpered to the correct pins of the RS232 connector 34. In this way, both DB25 and DB29 connectors can be used with the device.

Figure 4:
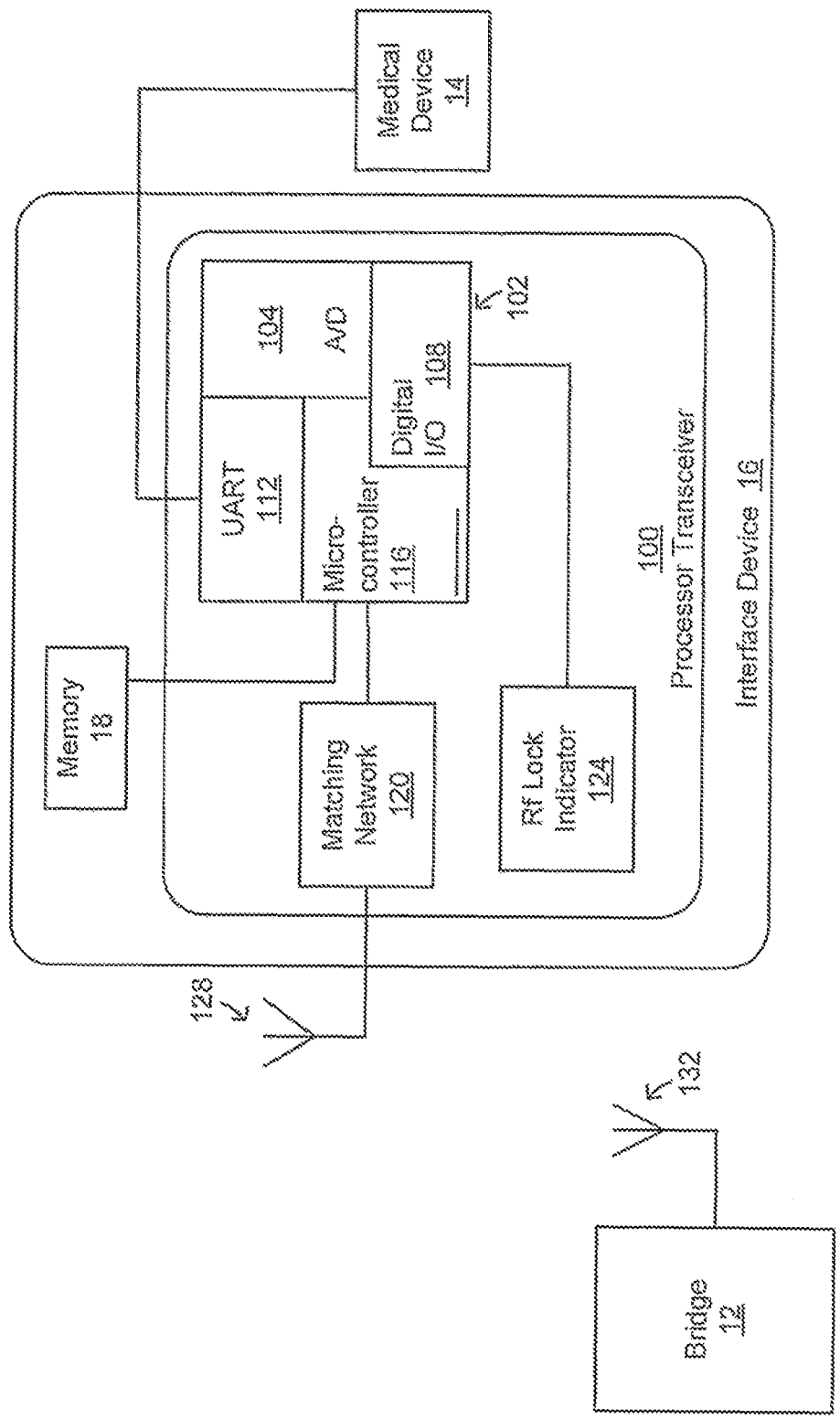
FIG. 4 is a block diagram of a system for connecting a bridge and an medical device through an interface device, according to an embodiment of the present invention.

In another embodiment, as shown in FIG. 4, the medical device 14 communicates with the bridge 12 wirelessly through a wireless interface device 16 having an antenna 128 and a processor-transceiver 100. As noted above, the bridge 12 then communicates through the network to the computer. In general, serial data signals containing medical device data passing from the medical device 14 enter the processor-transceiver 100 for conversion to USB signals. However, as noted above, for some medical devices, the medical device data cannot be converted to bridge data that the bridge 12 can process unless the data is recognized and converted by the processor-transceiver 100. Instructions on how to convert and modify the medical device data (such as RS232 serial data) into bridge data (such as USB data) are stored in the memory 18, which is electrically connected to the processor-transceiver 100. The instructions are provided to the processor-transceiver 100 when the interface device 16 is initially powered on. Then the interface device 16, shown in FIG. 4, wirelessly transmits the data to the bridge 12.

In the embodiment shown in FIG. 4, the processor-transceiver 100 contains an nRF24E1 processor 102 made by Nordic Semiconductor ASA (Tiller, Norway). The processor 102 has a 2.4 GHz RF transceiver with an embedded 8051 micro-controller 116, a multi-channel 12 bit A/D converter 104, a universal asynchronous receiver/transmitter ("UART") 112, and a digital I/o port 108. The processor 102 is a clock based processor, which operates at 1.9 volts, and has no external bus. The medical device 14 passes the data to the processor 102 as serial data through the UART 112.

The Nordic nRF24E1 processor 102 provides the encoded output signal to the transceiver portion for transmission by the Nordic nRF24E1 processor 102 to the antenna 128 through the matching network 120. The matching network 120 to impedance matches the antenna 128. The transceiver portion of the processor 102 can be set to operate on any one of 80 frequencies in the 2.4 GHz ISM band. Finally, the integral digital I/O portion 108 produces an output signal to the RF lock indicator 124 that the RF frequency has been detected and is locked onto.

In operation the first step is the storing in the memory 18 of device communication data that instructs the processor-transceiver 100 how to communicate with the medical device 14. Typically, the communication data is stored on the interface device 16 prior to the interface device 16 being attached to the medical device 14. For example, a hospital technician identifies that an interface device 16 will be connected to a ventilator and programs the device communication data into the memory 18 of the interface device 16. For example, the data and protocol enables the interface device 16 to convert the ventilator data into a form that is readable by the bridge 12 and a computer system.

Once the interface device 16 has the necessary communication data stored in its memory to permit the bridge 12 to communicate with the medical device 14, the interface device 16 begins receiving device data from the medical device 14. Once the interface device 16 starts receiving the medical device data, the processor-transceiver 100 of the interface device 16 begins using the stored data and protocol to convert the medical device data received from the medical device 14 to permit the medical device 14 to communicate with the bridge 12. Once the processor-transceiver 100 has converted the medical device data to data readable by the bridge, the processor-transceiver 100 transmits that bridge readable data to the bridge wirelessly.

In order to communicate wirelessly with the bridge 12, the processor-transceiver 100 initially can be in a listen mode at a predefined frequency. The bridge 12 broadcasts on this predetermined frequency, the value of the frequency it will be expecting to transmit and receive on. The processor-transceiver 100 at time zero, will operate in receive mode on channel 0 looking for a response. The processor-transceiver 100 will not transmit on any channel until a signal is detected from the bridge 12. The processor-transceiver 100 then switches itself to the transmit-and-receive frequency expected by the bridge 12. At this point the bridge 12 instructs the processor-transceiver 100 to collect and transmit data. After each transmission from the processor-transceiver 100, the bridge 12 issues an acknowledgement (ACK). If the processor-transceiver 100 fails to receive an ACK it returns to listen mode to determine if the bridge 12 has changed transmission frequencies.

Figure 5:
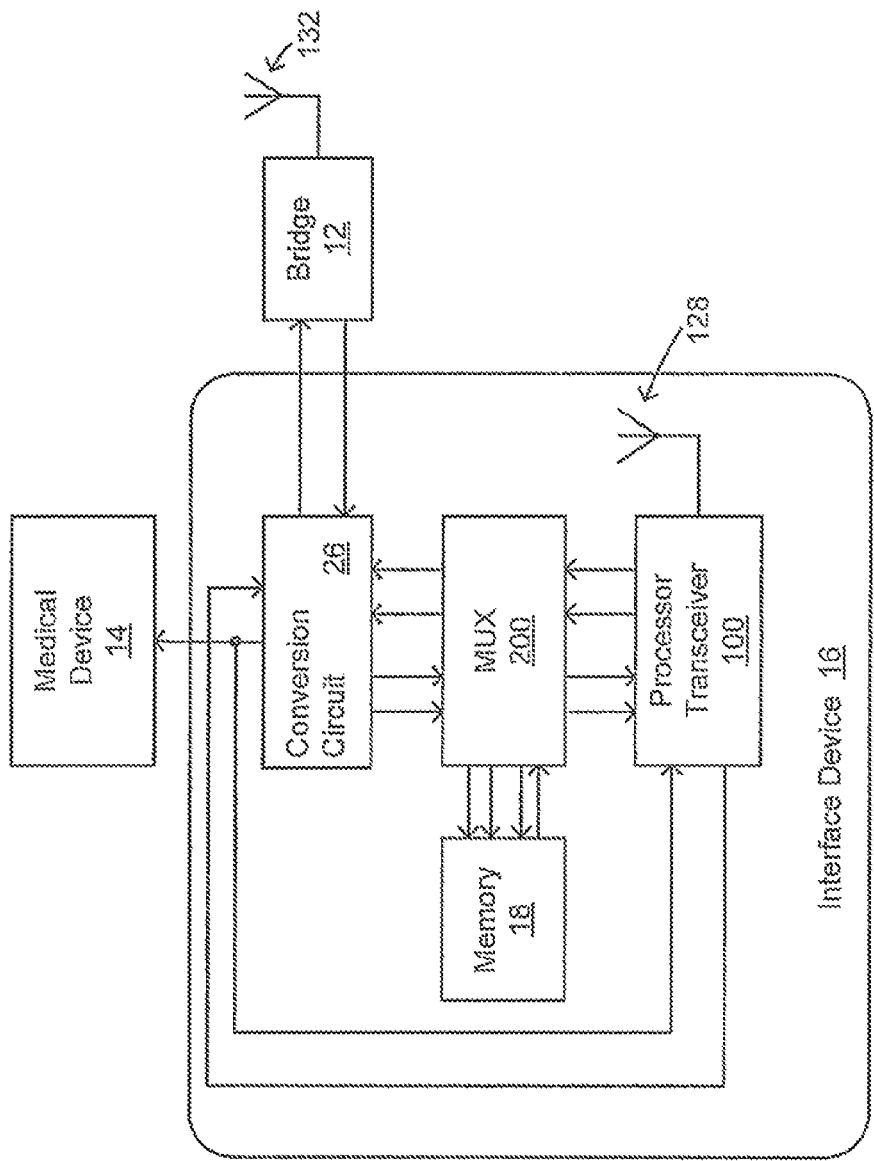
FIG. 5 is a block diagram of a system for connecting a bridge and a medical device.

In another embodiment, as shown in FIG. 5, the interface device 16 includes both a wired and wireless communication options. The medical device is electrically connected to both the conversion circuit 26 and the processor-transceiver 100. In this embodiment, the information collected by the medical device 14 can be transmitted through a USB cable via the conversion circuit 26 or wirelessly through the processor-transceiver 100 to the bridge 12. This system includes a multiplexer (MUX) 200, in. electrical communication with the conversion circuit 26 and the processor-transceiver 100. The MUX 200 also can be electrically connected to the memory 18. The MUX operates to either transmit data from conversion circuit 26 to the MUX 200 and then to the memory 18, or from the processor-transceiver 100 to the MUX 200 and then to the memory 18.

When the conversion circuit 26 is being used to transmit data to the bridge 12, the medical device sends data to the conversion circuit 26. The conversion circuit 26 then communicates with the MUX 200. The MUX 200 then accesses the memory 18. As discussed above, the memory 18 is programmed to identify and communicate with various electronic devices. Thus, through the MUX 200, the conversion circuit 26 can access the memory 18 to convert the data from the medical device 14 into data that can be read and processed by the bridge 12. Finally, the conversion circuit 26 transmits the processed information to the bridge 12.

When the processor-transceiver 100 is being used to transmit data wirelessly to the bridge 12, the medical device 14 is electrically connected to the processor-transceiver 100. The processor-transceiver 100 receives serial data from the medical device 14. The MUX 200 permits communication between the processor-transceiver 100 and the memory 18. Through communication with the memory 18, the processor-transceiver 100 can take the medical device data and convert the medical device data into data that can be read and processed by the bridge. An antenna 128 is connected to the processor-transceiver 100 to transmit the converted data wirelessly to an antenna 132 associated with the bridge 12.

Variations, modification, and other implementations of what is described herein will occur to those of ordinary skill in the art without departing from the spirit and scope of the invention as claimed. Accordingly, the invention is to be defined not by the preceding illustrative description, but instead, by the spirit and scope of the following claims.

What is claimed is:

1. An electrically isolated medical device data converter comprising:
   a serial line interface for connection to a medical device serial port, the medical device having a medical device data protocol;
   an isolation circuit having an isolation circuit input bus in electrical communication with the serial line interface and having an isolation circuit output bus;
   a protocol conversion circuit having a protocol conversion circuit output bus and a protocol conversion circuit input bus in electrical communication with the isolation circuit output bus;
   a USB interface in electrical communication with the protocol conversion circuit output bus; and
   a programmable memory having a memory output bus,
   wherein the protocol conversion circuit further comprises a protocol conversion circuit memory bus in electrical communication with the memory output bus,
   wherein the protocol conversion circuit identifies the medical device connected to the isolated medical device data converter; and
   wherein the programmable memory provides protocol conversion data to the protocol conversion circuit to permit the protocol conversion circuit to convert the medical device data protocol to a protocol for communication through the USB interface based on the medical device identification.

2. The electrically isolated medical device data converter of claim 1 further comprising:
   an isolated power supply providing power to components of the electrically isolated medical device data converter while electrically isolating the USB interface from the serial line interface.

3. The electrically isolated medical device data converter of claim 1 wherein the serial interface is an RS232 interface.

4. The electrically isolated medical device data converter of claim 1 wherein the isolation circuit comprises a serial line isolator and a digital isolator connected by a bus.

5. The electrically isolated medical device data converter of claim 1 wherein the memory is an EE PROM.

6. The electrically isolated medical device data converter of claim 1 further comprising an isolated power supply is a regulated power supply.

7. The electrically isolated medical device data converter of claim 6 further comprising a power switch enable circuit in communication between the protocol conversion circuit and the isolated power supply.

8. A method of converting medical device data from a medical device having a medical device data protocol, the method comprising the steps of:
   loading medical device protocol information into a programmable memory;
   receiving the medical device data from the medical device through a serial line interface;
   passing the medical device data with the medical device data protocol from the serial line interface through an electrical isolation circuit;
   identifying, using a protocol conversion circuit, the medical device connected to the serial line interface;
   reading, using the protocol conversion circuit, medical device protocol conversion information from the programmable memory based on the identification of the medical device;
   and
   converting, using the protocol conversion circuit, the medical device data having the medical device data protocol to medical data comprising a USB protocol using the medical device protocol conversion information read from memory.

9. An electrically isolated medical device data converter comprising:
   a serial line interface for connection to a medical device serial port, the medical device having a medical device data protocol;
   an isolation circuit having an isolation circuit input bus in electrical communication with the serial line interface and having an isolation circuit output bus;
   a protocol conversion circuit having a protocol conversion circuit output bus and a protocol conversion circuit input bus in electrical communication with the isolation circuit output bus;

an output interface in electrical communication with the protocol conversion circuit output bus; and a user programmable memory having a memory output bus, and wherein the protocol conversion circuit further comprises a protocol conversion circuit memory bus in electrical communication with the memory output bus, wherein the protocol conversion circuit identifies the medical device connected to the isolated medical device data converter; and wherein the memory provides protocol conversion data to the protocol conversion circuit to permit the protocol conversion circuit to convert the medical device data protocol to a protocol for communication through the output interface based on the medical device identification.

10. The electrically isolated medical device data converter of claim 9 further comprising:

an isolated power supply providing power to components of the electrically isolated medical device data converter while electrically isolating the output interface from the serial line interface.

* * * * *